(12) United States Patent
Miura et al.

(10) Patent No.: US 6,491,658 B1
(45) Date of Patent: Dec. 10, 2002

(54) AUTOMATED SOLUTION INJECTION-DISCHARGE SYSTEM AND AUTOMATED PERITONEAL DIALYSIS SYSTEM

(75) Inventors: Hiromu Miura, Hiroshima (JP); Katsuya Yamashita, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 09/518,258

(22) Filed: Mar. 3, 2000

Related U.S. Application Data

(62) Division of application No. 09/342,055, filed on Jun. 29, 1999.

(51) Int. Cl.⁷ .............................................. A61M 1/00
(52) U.S. Cl. ...................................................... 604/29
(58) Field of Search ............................ 604/28–31, 4.01, 604/5.01, 5.04, 6.12, 6.15, 6.16; 210/645–47, 321.71

(56) References Cited

U.S. PATENT DOCUMENTS 3,520,298 A * 7/1970 Lange
3,709,222 A    1/1973 DeVries .................. 604/28
4,585,436 A * 4/1986 Davis et al. ............. 604/29
4,586,920 A * 5/1986 Peabody ................. 604/29
4,747,822 A * 5/1988 Peabody ................. 604/29
4,840,621 A    6/1989 Larkin et al. ............ 604/29
5,338,293 A * 8/1994 Jeppsson et al. ......... 604/29
5,474,683 A   12/1995 Bryant et al. ............ 210/646
5,641,405 A    6/1997 Keshaviah et al. ....... 210/645
5,776,091 A * 7/1998 Brugger et al. .......... 604/4
5,783,072 A    7/1998 Kenley et al. .......... 210/195.2
5,938,634 A    8/1999 Packard ................. 604/29
5,980,481 A * 11/1999 Gorsuch ................ 604/28

* cited by examiner

Primary Examiner—Michael J. Hayes
Assistant Examiner—Kevin C. Sirmons
(74) Attorney, Agent, or Firm—Armstrong, Westerman, & Hattori, LLP

(57) ABSTRACT

The automated solution injection-discharge system is used as an APDS system to supply and discharge a dialysate and a patient's drain. And an automated solution injection-discharge system provides free of contamination and operation mistakes, and can accurately control the injected dialysate volume and the discharged dwell solution volume even when a patient does not maintain a fixed posture while replacing the solution.

27 Claims, 9 Drawing Sheets

Figure 1:
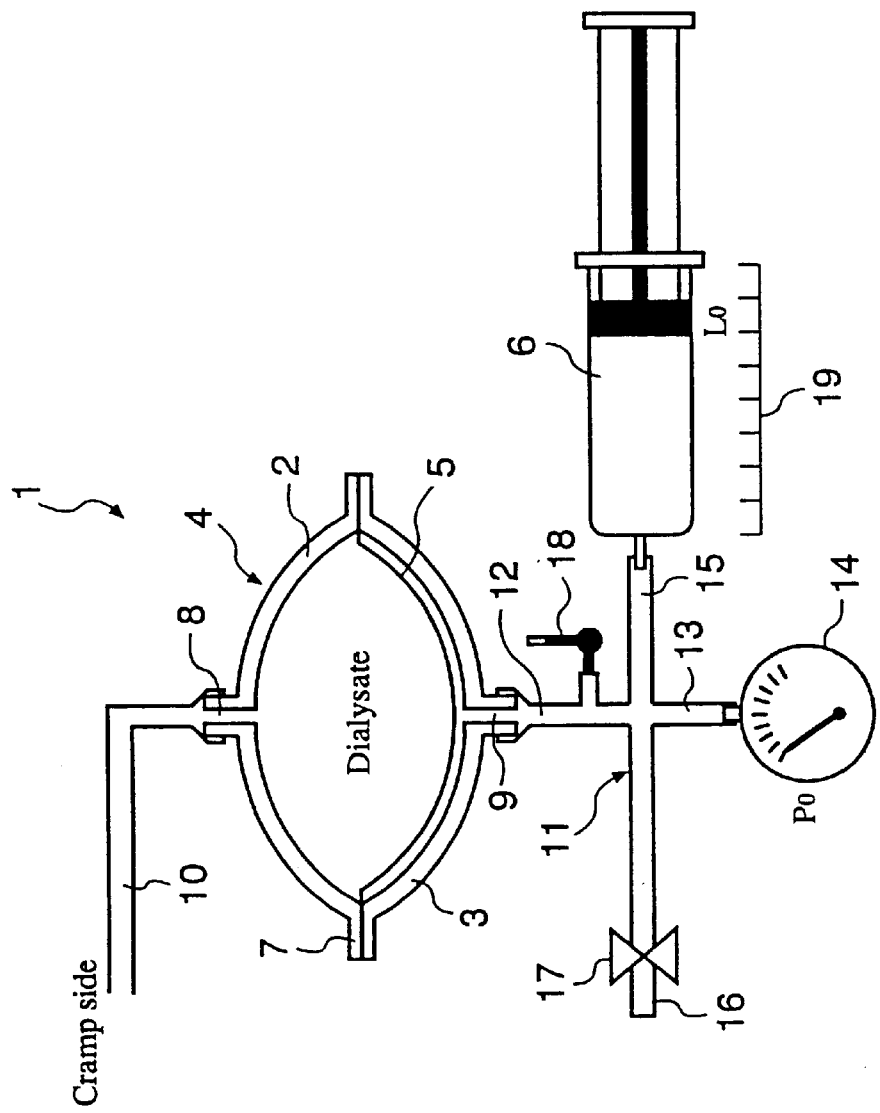

AUTOMATED SOLUTION INJECTION-DISCHARGE SYSTEM AND AUTOMATED PERITONEAL DIALYSIS SYSTEM

This application is a division of prior application Ser. No. 09/342,055 filed Jun. 29, 1999.

BACKGROUND OF THE INVENTION

The present invention relates to an automated solution injection-discharge system which automatically injects a dialysate into a patient's peritoneal cavity and discharges the dialysate after the appointed time. In addition, the present invention relates to an automated peritoneal dialysis system (APDS) which employs the above-mentioned automated solution injection-discharge system.

Dialytic treatment has advantages such as (1) medical expenses are inexpensive, (2) the patient does not require frequent outpatient treatment, and (3) the patient can easily return to society. As a result, medical facilities in Japan have increasingly introduced dialytic treatment.

In continuous ambulatory peritoneal dialysis (CAPD), a patient can easily replace the dialysate at home at moderate cost. Many peritoneal dialytic patients have recently received CAPD treatment. In this treatment, however, a patient has to exchange bags several times, desorb connectors, and open and close a clamp (a closing gear) every day, which is troublesome to the patient.

An operating mistake by a patient, especially by a sight-or hand-impaired patient, may contaminate the connector of the dialytic system. Moreover, a user may make mistakes in injecting and discharging.

Based on the weak points above, the peritoneal dialysis system with automatic operation has been developed and improved. A conventional peritoneal dialysis system has adopted a method in which a dialysate is injected, by the head drop, into a patient's peritoneal cavity and discharged from a patient's peritoneal cavity.

This type of peritoneal dialysis system is relatively simple in structure. Moreover, the mechanism is safe and gentle to the living body because the dialysate is injected and discharged by gravitation.

However, the head drop mechanism has some demerits in that the patient must maintain a fixed posture, and the system is relatively large in size.

As a countermeasure against these, a roller pump is used to inject and discharge a solution in the peritoneal dialysis system. A system with a roller pump requires no head drop. However, there is a possibility that dialysate may be excessively injected into a patient because the roller pump may rotate without reference to the prescribed volume of solution. Another possibility is that the peritoneum may be damaged if the roller pump automatically sucks when a small amount of dialysate remains in the peritoneal cavity. The conventional solution injection-discharge system has merits and demerits as mentioned above. Other demerits are as f follows. First, the system is large in size and expensive because a load cell weighs the filled and drained volumes of solution.

Second, the control system is complicated and expensive because each closing gear, which is installed on each conduit connected between a dialysate bag, a drain bag, a patient's peritoneal catheter, a warming gear, and a reservoir for compounding and warming a solution, operates separately.

SUMMARY AND OBJECTS OF THE INVENTION

The first object of the present invention is to provide a compact, simple-structured, and user-friendly automated solution injection-discharge system ensuring safe operation of injected and discharged solution. Especially when the automated solution injection-discharge system is used as an APDS system to supply and discharge a dialysate and a patient's drain, the object is to provide an automated solution injection-discharge system (1) which is free of contamination and operation mistakes, and (2) which can accurately control the injected dialysate volume and the discharged dwell solution volume even when a patient does not maintain a fixed posture while replacing the solution.

The second object of the present invention is to provide an automated peritoneal dialysis system (hereinafter referred to as APDS) which operates in a set order and lessens manual operations for replacing a dialysate. The third object is to provide a compact, simple-structured, and low-cost APDS.

An automated solution injection-discharge system according to the invention comprise: (1) a chamber which is provided with a gas opening to introduce or exhaust a gas at one end of the chamber, and a solution opening to suck or discharge a solution at the other end; (2) a diaphragm installed in the chamber, which divides the chamber into a room with the gas opening and a room with the solution opening, for sucking a solution into the chamber or discharging a solution from the chamber by introducing or exhausting a gas through the gas opening; (3) a driving device which drives the diaphragm; (4) a measuring device which detects the volume of a solution sucked into or discharged from the chamber, and the volume of air sucked into or exhausted from the chamber; and (5) an air-pressure sensor which detects the pressure in a tube to supply or suck air into the chamber; wherein, by sucking a gas into the chamber through the gas opening, the diaphragm is inverted to the side of the gas opening to suck a solution into the chamber, and by introducing a gas into the chamber through the gas opening, the diaphragm is inverted to the side of the solution opening to discharge a solution from the chamber.

The driving device is provided with any one of the driving device such as an air cylinder, a piston and cylinder, and a flexible bag.

The volume of the air cylinder is 1.4 to 2.0 times the volume of the chamber.

The measuring device is a position detecting sensor which is installed near the driving device.

The automated solution injection-discharge system is used for an automated peritoneal dialysis system.

An automated peritoneal dialysis system accordong to the invention comprises: a dialysate container; a reservoir to contain a dialysate before it is injected into a patient's peritoneal cavity; a drain container to contain a drain from a patient's peritoneal cavity;an automated solution injection-discharge system to suck and supply dialysate and drain; said automated solution injection-discharge system being provided with the following (1) to (5):(1) a chamber which is provided with a gas opening to introduce and exhaust a gas at one end of the chamber, and a solution opening to suck or discharge a solution at the other end; (2) a diaphragm installed in the chamber, which divides the chamber into a room with the gas opening and a room with the solution opening for sucking a solution into the chamber or discharges a solution from the chamber by introducing or exhausting a gas through the gas opening; (3) a driving device to drive the diaphragm; (4) a measuring device which detects the volume of solution sucked or discharged by the chamber, and the volume of gas sucked into or exhausted from the chamber; and(5) an air-pressure sensor which detects the pressure in a tube to supply or suck a gas into the chamber; a manifold connected to the automated solution injection-discharge system; plural conduits connected between the manifold and the containers: and conduit swiching device to open and close the conduits.

An automated peritoneal dialysis system according to the invention comprises:a dialysate container; a reservoir to contain a dialysate before it is injected into a patient's peritoneal cavity; a drain container to contain a drain from a patient's peritoneal cavity; and an automated solution injection-discharge system which sucks and supplies dialysate and drain; said automated solution injection-discharge system being provided with:a piston and a cylinder; a measuring means which measures the volume of solution sucked into or discharged from the cylinder, and the volume of air sucked into or exhausted from the cylinder; and an air-pressure sensor which detects the pressure in a tube to introduce or suck an air into the cylinder; a manifold which is connected to the automated solution injection-discharge system; plural conduits connected between the manifold and the containers; and conduit swiching device to open and close the conduits.

An automated peritoneal dialysis system according to the invention comprises:a dialysate container; a reservoir to contain a dialysate before it is injected into a patient's peritoneal cavity; a drain container to contain a drain from a patient's peritoneal cavity; an automated solution injection-discharge system which sucks and supplies dialysate and drain; said automated solution injection-discharge system being provided with:a flexible bag; a measuring means which detects the volume of solution sucked into or discharged from the flexible bag, and the volume of gas sucked into or discharged from the flexible bag; and an air-pressure sensor which detects the pressure in a tube to supply or introduce air into the flexible bag; a manifold connected to the automated solution injection-discharge system; plural conduits connected between the manifold and the containers; and conduit closing gears to open and close the conduits.

The plural dialysate containers, each container having a dialysate of different density are provided with.

The peritoneal catheter in the patient and/or at least a part of the conduit connected to the catheter are made from a flexible thin film.

The automated solution injection-discharge system is aseptically structured.

The pressure sensor detects the volume of dwell solution discharged so that the pressure in the peritoneal cavity is not sufficiently negative to damage a living body.

The speed of movement of the air cylinder piston is 10 to 200 ml/min, preferably 150 ml/min, for discharging a solution from a patient's peritoneal cavity, and the speed of injection of a solution is 20 to 400 ml/min, preferably 300 ml/min.

The conduit swiching device comprises:a rotating shaft; and swiching device which are provided with: an interlocking cam installed on the rotating shaft; a thrust device which moves up and down with the rotation of the interlocking cam; and a cradle which receives the head of the thrust device; wherein the number of rotating shafts is more few than the number of conduit swiching means.

The conduit swiching device are equipped with plural rotating shafts, said shafts having two or three conduit swiching means.

The conduit swiching means are provided with two rotating shafts, of which the first rotating shaft has three sets of conduit swiching means, and the second rotating shaft has two sets of conduit swiching means.

The three sets of conduit swiching neans on the first rotating shaft have a phase difference of 120 degrees, and the two sets of conduit swiching means on the second rotating shaft have a phase difference of 120 to 180 degrees.

An automated peritoneal dialysis system according to the invention comprises:a dialysate container; a reservoir to contain a dialysate before it is injected into a patient's peritoneal cavity; a drain container to contain a drain from a patient's peritoneal cavity; an automated solution injection-discharge system which sucks and supplies dialysate and drain; a manifold connected to the automated solution injection-discharge system; plural conduits connected between the manifold and the containers and the patient; and a conduit swiching device to open and close the conduits; said conduit swiching device being equipped with swiching means which are driven by rotating shafts, the number of which is more few than the number of swiching means.

An automated peritoneal dialysis system according to the invention comprises: a dialysate container; a reservoir to contain a dialysate before it is injected into a patient's peritoneal cavity; a drain container to contain a drain from a patient's peritoneal cavity; an automated solution injection-discharge system which sucks and supplies dialysate and drain; a manifold which is connected to the automated solution injection-discharge system; plural conduits which connect between the manifold and the containers and the patient; a conduit swiching device to open and close the conduit; a measuring means which detects the volume of solution sucked into or discharged from a chamber, and the volume of air sucked into or exhausted from the chamber; and a pressure sensor which detects the pressure in a tube to introduce air into the chamber; said pressure sensor detecting the volume of dwell solution discharged so that the pressure in the peritoneal cavity is not sufficiently negative to damage a living body.

BRIEF DESCRIPTIONS OF THE DRAWINGS

Figure 2:
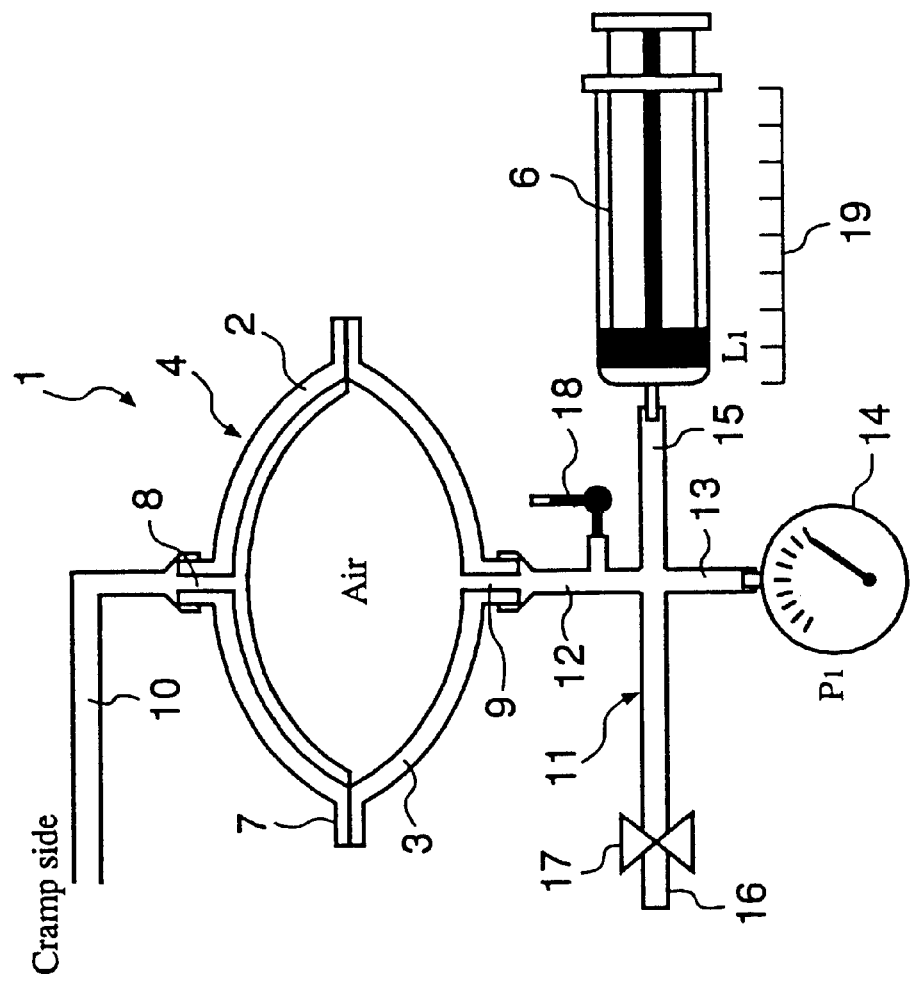

FIGS. 1 and 2 schematically show the automated solution injection-discharge system of the present invention.

Figure 3:
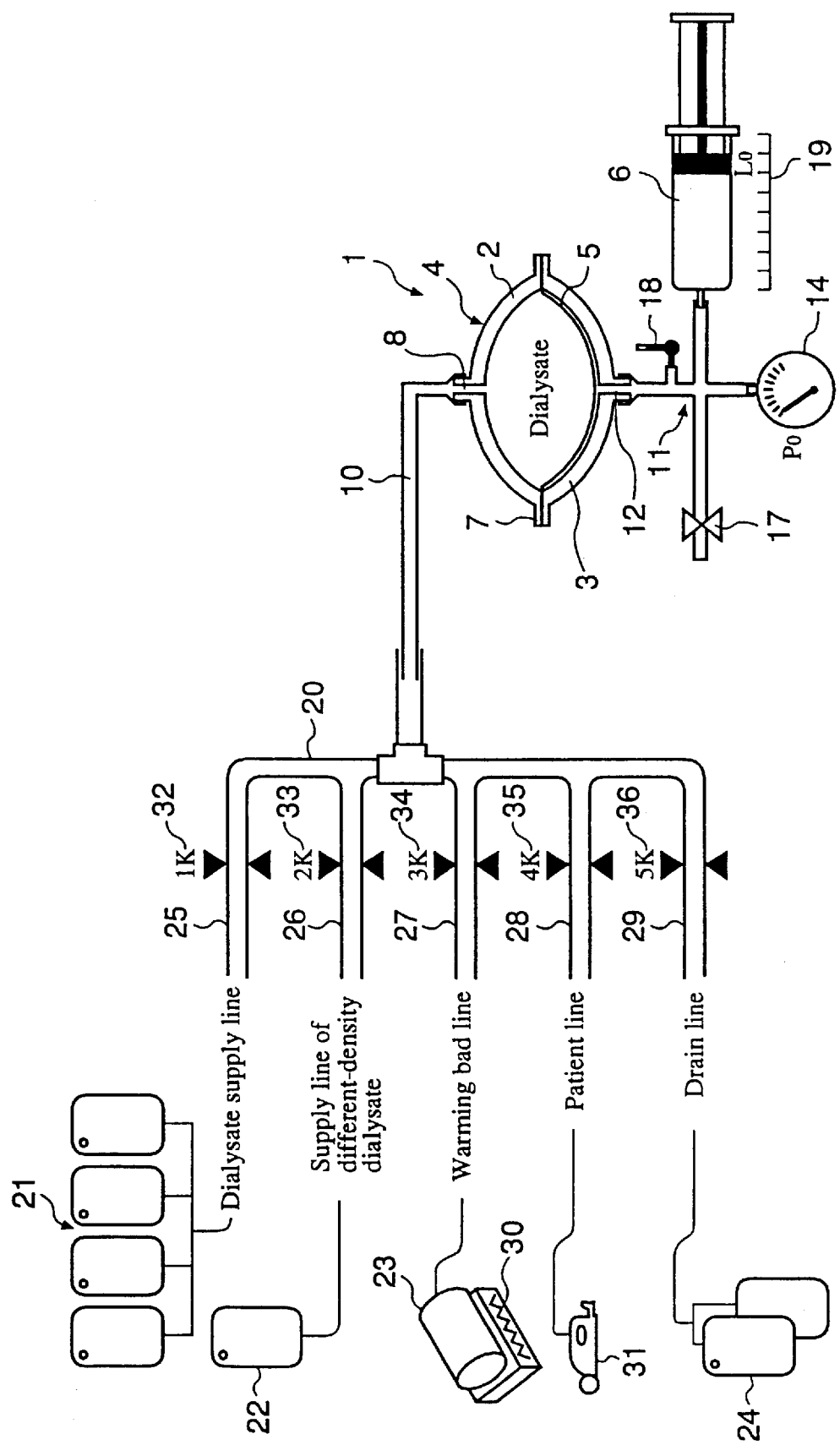

FIG. 3 schematically shows an APDS employing the automated solution injection-discharge system of FIG. 1.

Figure 4A:
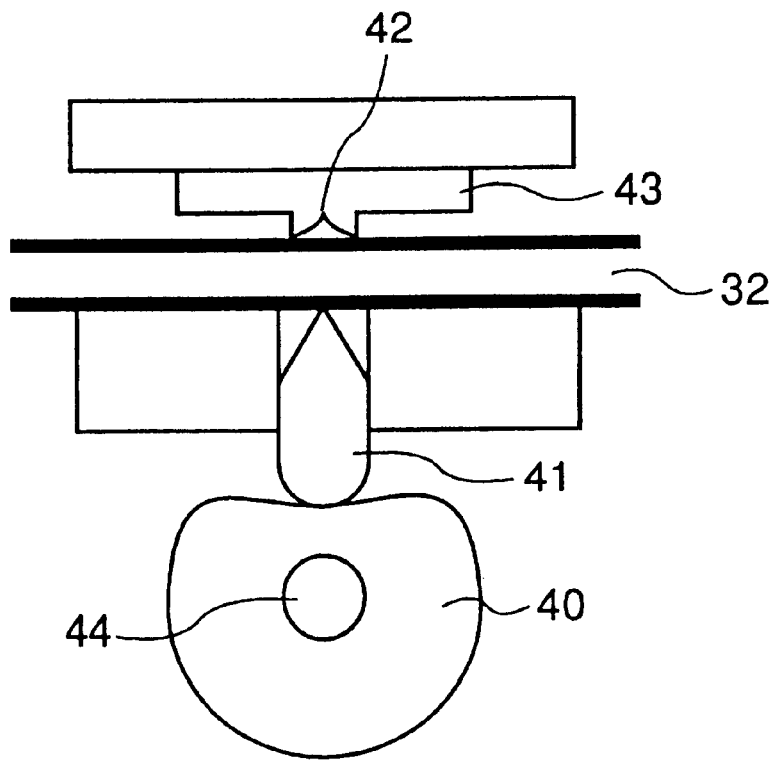
Figure 4B:
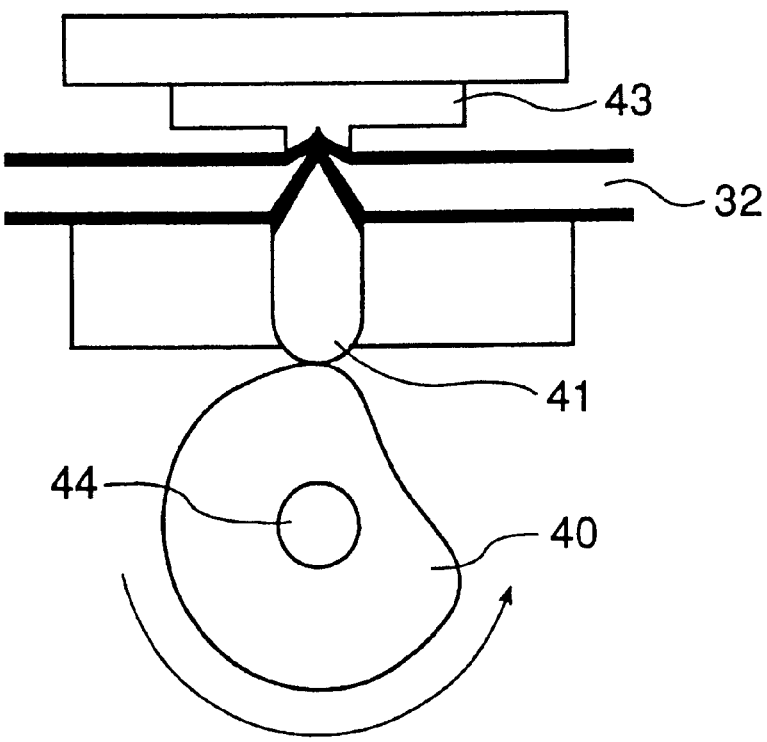

FIGS. 4(A) and(B) schematically show the conduit swiching device. FIG. 4(A) shows an opened conduit, and FIG. 4(B) shows a closed conduit.

Figure 5:
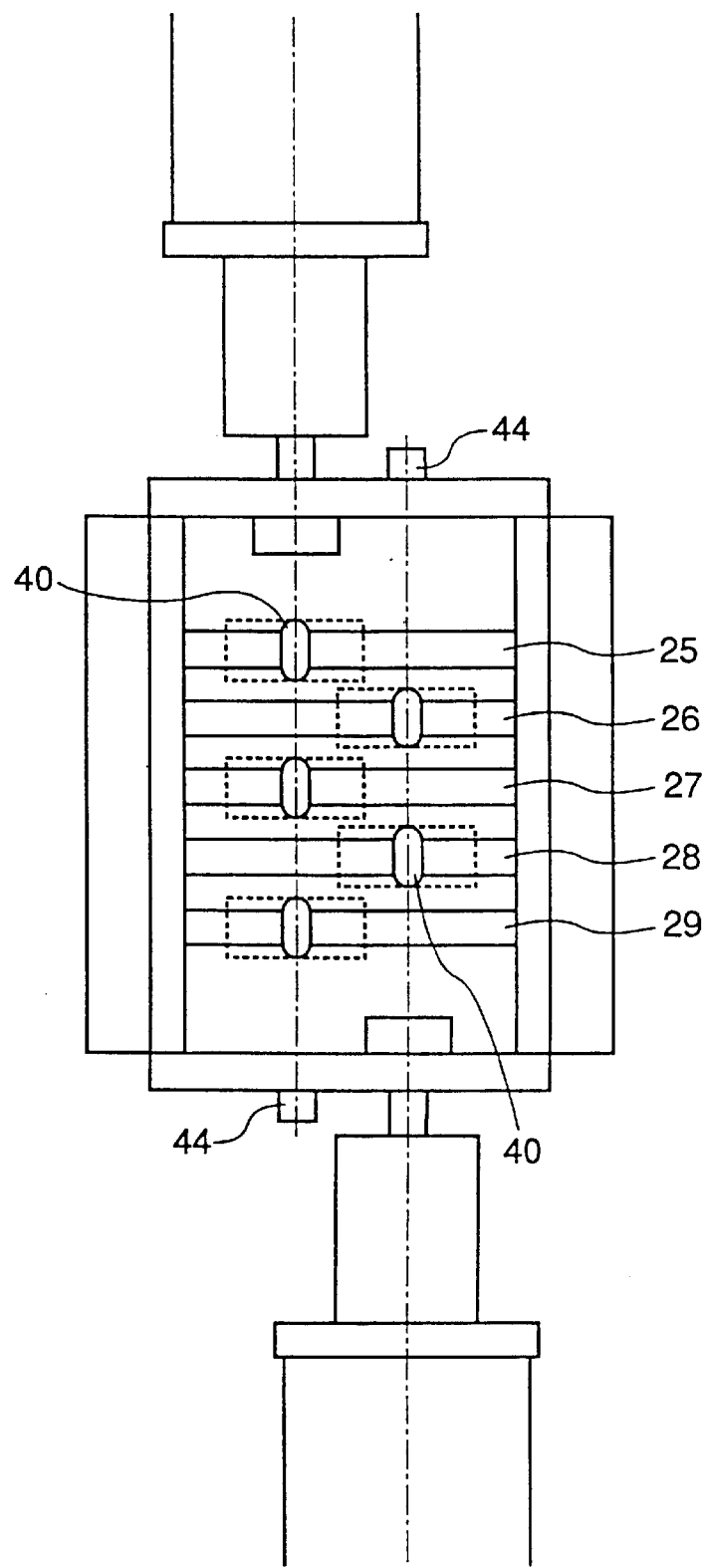

FIG. 5 shows a conduit swiching device on the rotating shaft of an APDS.

Figure 6:
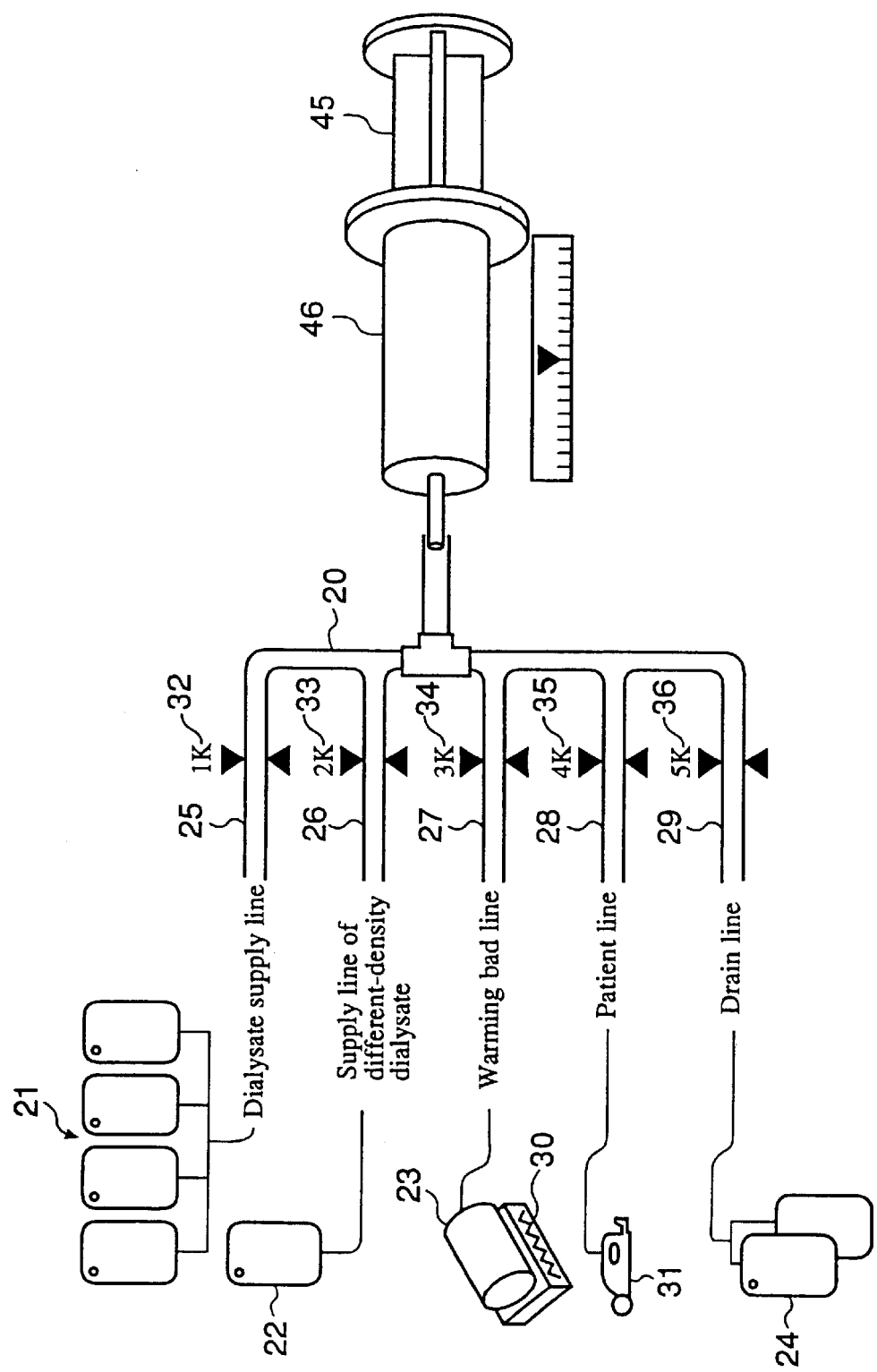

FIG. 6 schematically shows an APDS employing another automated solution injection-discharge system.

Figure 7:
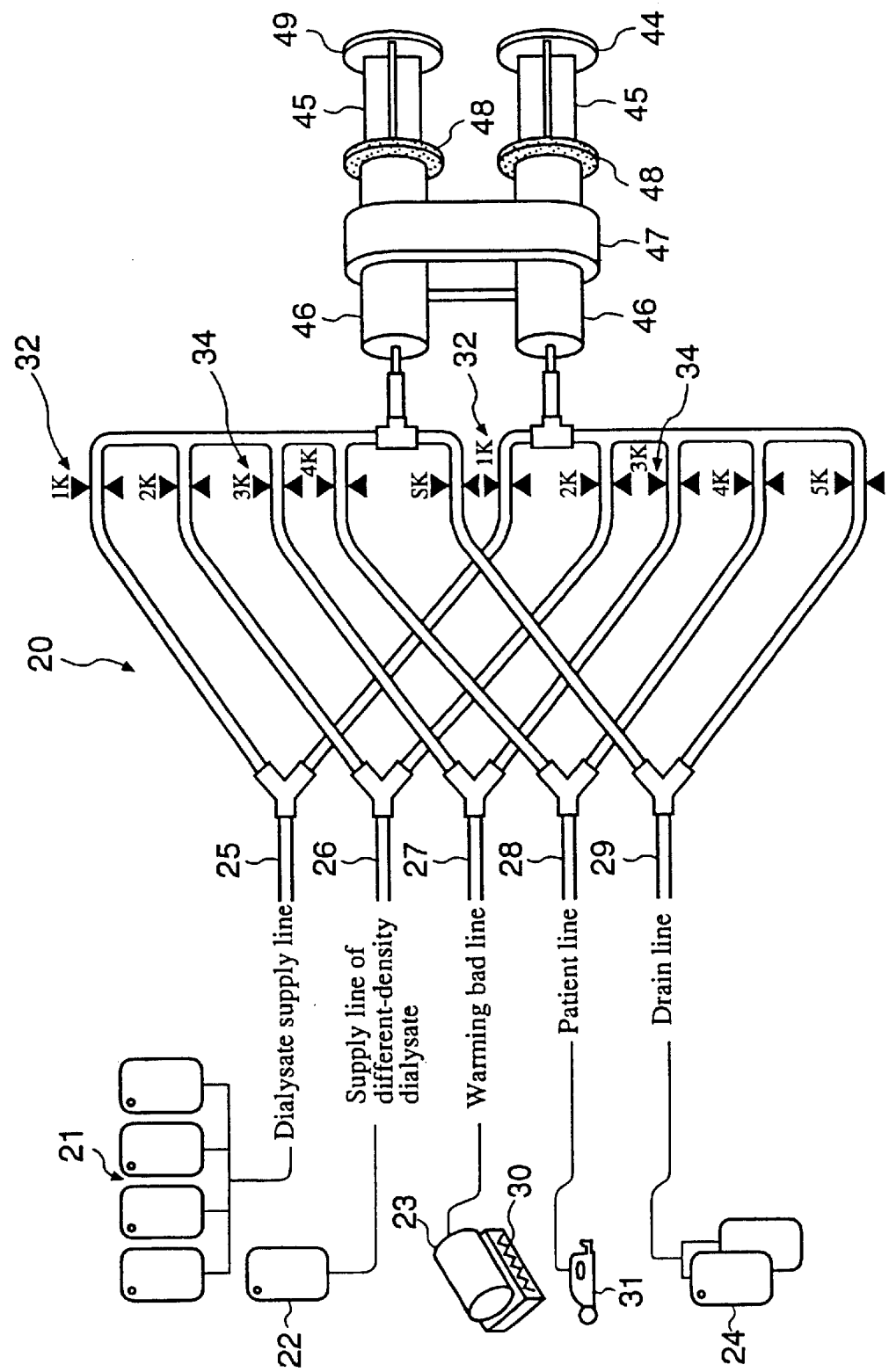

FIG. 7 schematically shows an APDS employing the other automated solution injection-discharge system.

Figure 8:
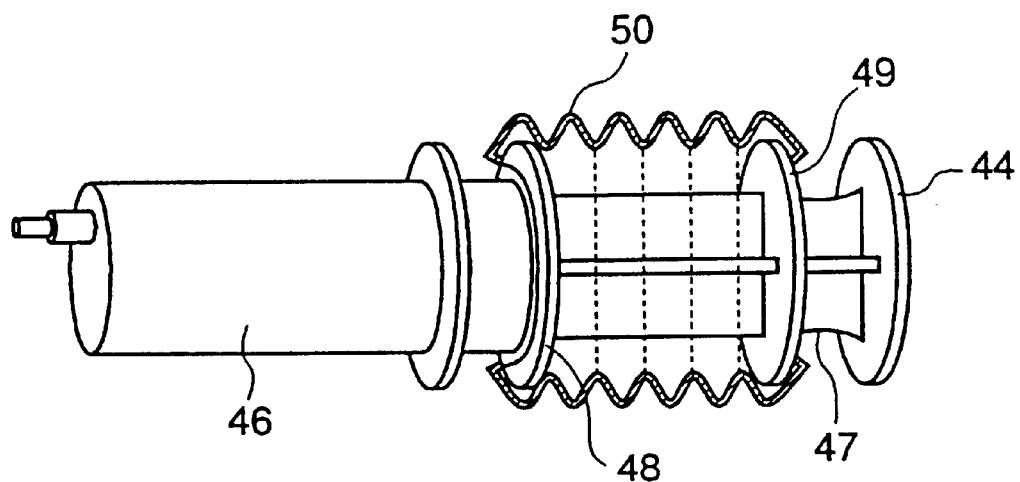
Figure 9:
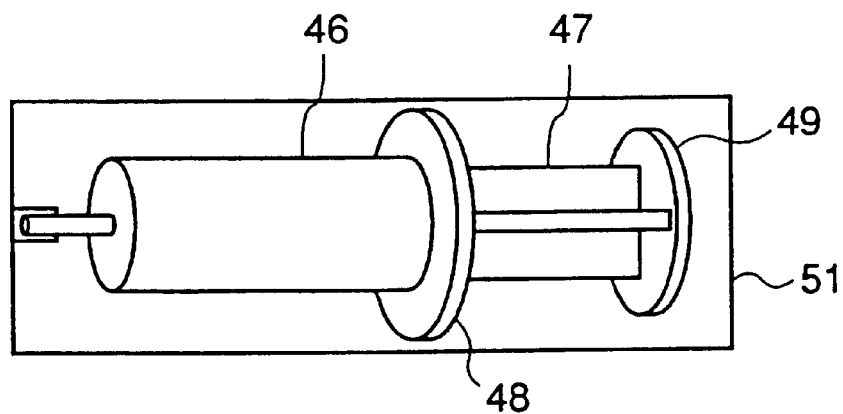

FIGS. 8 and 9 schematically show the aseptically structured cylinder.

Figure 10:
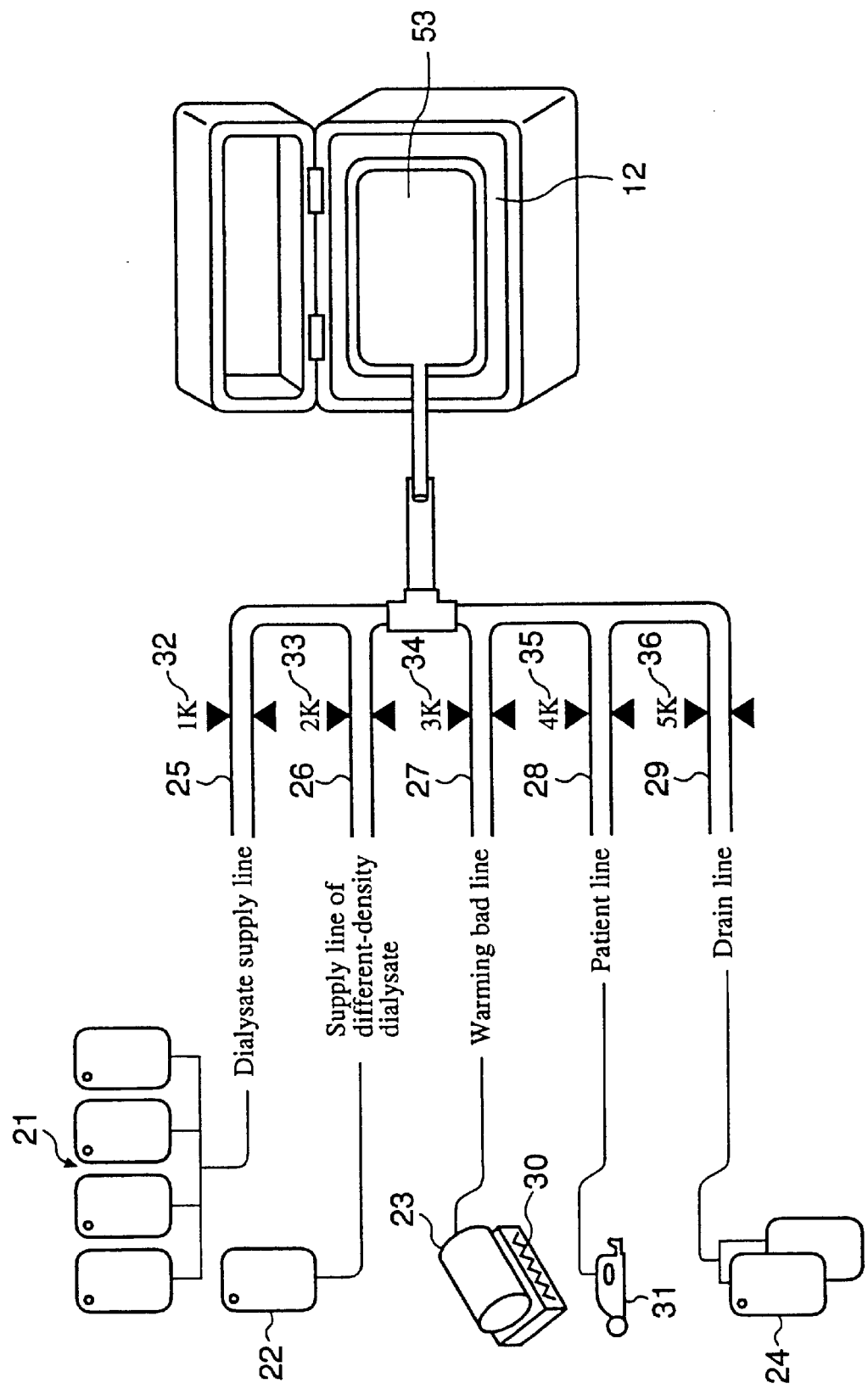

FIG. 10 schematically shows an APDS employing the other automated solution injection-discharge system.

DETAILED DESCRIPTION OF THE INVENTION

A detailed description of the invention is provided based on the drawings.

FIGS. 1 and 2 outline the automated solution injection-discharge system of the APDS, using a diaphragm related to the present invention that sucks or introduces a peritoneal dialysate or a drain from a peritoneum. In FIG. 2, the diaphragm of FIG. 1 is inverted to the upper position. In FIGS. 1 and 2, the numbers are identical for the same machine configurations.

In FIG. 2, automated solution injection-discharge system 1 is provided with a chamber 4 equipped with a hemispherical top cover 2 and a hemispherical bottom cover 3, a diaphragm 5 installed in chamber 4, and a driving device 6 to move diaphragm 5. Diaphragm 5 is made of a synthetic resin thin film such as silicone, vinyl chloride resin, natural rubber, thermoplastic elastomer, or other materials. The diaphragm is ordinarily approximately 0.2 to 0.5 mm in thickness. Top cover 2 and bottom cover 3 are preferably made of hard transparent plastic such as polycarbonate, vinyl chloride resin, polypropylene, or other materials.

A rim flange of the top and bottom covers is provided with a jut 7, which runs outwards from the rim flange of chamber 4. The rim flange of diaphragm 5 is fixed at jut 7 of both covers, and the diaphragm is held in the chamber. Jut 7 is fixed by a fixative such as an inserter, welder, or screws (not shown).

On top cover 2 is a solution opening 8 to introduce and discharge a solution. On bottom cover 3 is a gas opening 9 to introduce and exhaust a gas. Solution opening 8 is 5 mm in diameter. Gas opening 9 is 4 mm in diameter. The maximum diameter of chamber 4, which is composed of covers 2 and 3, is 76 mm. When the automated solution injection-discharge system is used as the chamber for the APDS, the chamber volume is ordinarily 10 to 100 cc, preferably 20 to 50 cc.

Solution opening 8 is connected to a tube 10 which introduces and discharges a solution. Gas opening 9 is connected to a tube 11 which is branched into four. The first end 12 of the branched tubes is connected to gas opening 9. The second end 13 of the branched tubes is connected to an air-pressure sensor 14. The third end 15 is connected to a driving device 6 (an air cylinder). The fourth end 16 is connected to an air bulb 17. Reference No. 18 is a temperature sensor.

As mentioned above, the air cylinder is used as a driving device to invert the diaphragm up and down in the chamber. Moreover, an air-exhausting device such as an air pump can also be used as a driving device. The volume of the air cylinder is preferably 1.4 to 2.0 times the volume of the chamber.

More specifically, when the chamber volume is 50 cc, the diaphragm theoretically discharges 50 cc of solution by infusing 50 cc of air into the chamber. Moreover, diaphragm 5 can introduce 50 cc of solution into the chamber by exhausting 50 cc of air. However, when 50 cc of solution is fully introduced into the chamber, the diaphragm must adhere fast to the chamber inner wall. In this case, 70 to 100 cc of air, which is 1.4 to 2.0 times the chamber volume, should be exhausted. On the other hand, when 50 cc of solution is fully discharged from the chamber, 70 to 100 cc of air, which is 1.4 to 2.0 times the chamber volume, should be introduced. In short, the air cylinder must be larger in volume than the chamber. The air cylinder volume is preferably 1.4 to 2.0 times larger than the chamber volume.

In the APDS, other types of automated solution injection-discharge systems can be used instead of using a chamber equipped with a diaphragm. As shown in FIG. 6. for example, a cylinder and a piston which reciprocates axially in the cylinder can be used. As shown in FIG. 10, a flexible bag with a specified volume can be used. It is also possible to divide the chamber into two rooms by setting up a flexible diaphragm in the chamber.

Furthermore, it is preferable to install a measuring sensor which measures the volume of air sucked into or exhausted from the chamber, and which detects the sucked and discharged volume of a dialysate or a drain from a patient's peritoneal cavity. As an example, a position detecting sensor 19 is installed near the air cylinder. The position detecting sensor is a photo-sensor (a photo interrupter), a slider type resister (a potentiometer) or other devices. The measuring sensor detects the gas volume sucked into or exhausted from the chamber, to enable the solution fill and drain volume to be automatically controlled.

The following is the method to measure, with the use of an air cylinder, the dialysate volume introduced into a chamber or the drain volume discharged from a patient's peritoneal cavity. A photo-encoder is used as a position detecting sensor.

Measurement is conducted by an integer multiplication of the chamber volume. That is, when a chamber is 50 cc in volume, measurement is carried out by the multiplication of (50 cc x Number of reciprocating motions of air cylinder).

Photo-encoder 19 is used as a position detecting sensor. When the detection point L of photo-encoder 19 is at the longest stroke point L0 of cylinder, chamber 2 is assessed to be filled with dialysate. When the detection point L is at the shortest stroke point L1, chamber 2 is assessed to be filled with air after discharging dialysate (see FIGS. 1 and 2).

Additionally, when L is at L0, and when P0 fulfills the following requirements, the chamber is assessed to be filled with dialysate. When L is at L1, and when P1 fulfills the following requirements, the chamber is assessed to be filled with air after discharging dialysate. In this manner, safe and accurate measurement is conducted.

$$KA < P0 \leq KB$$

$$KC \leq P1 \leq KD$$

KA is a pressure rated value to determine that a solution cannot be sucked because a negative pressure is applied to the chamber; in other words, that a manifold-side flow pathway (a solution-side flow pathway) is closed or that a dwell solution is completely discharged from the peritoneal cavity.

KB and KC are pressure rated values to determine that the diaphragm is adhering fast to the chamber inner wall (in this case, however, no leakage is to be found in the chamber, diaphragm, or any flow pathways). KB herein is a negative pressure. KC is a positive pressure. KD and KA are pressure rated values to determine that some flow pathways are closed when the chamber pressure is positive.

KA, the sucking capacity of the solution injection-discharge system of the present invention, is ordinarily approximately $-4.0$ to $-1.5$ $kgf/cm^2$. KB is approximately $-0.7$ to $-1.0$ $kgf/cm^2$. KC is approximately 1.2 to 1.8 $kgf/cm^2$. KD is approximately 2.0 to 4.0 $kgf/cm^2$. The absolute value at under limit of KA and KD is the estimated pressure value of a patient line. The pressure value is set at a lower negative and positive pressure than the other lines.

It is preferable to install pressure sensor 14 between a chamber and an air cylinder, to monitor the pressure in a flow pathway through which air is pumped into a chamber.

FIG. 3 shows an APDS for sucking and infusing a peritoneal dialysate and a drain from a patient's peritoneal cavity, with the use of an automated solution injection-discharge system employing the diaphragm of FIG. 1.

In FIG. 3, an automated solution injection-discharge system 1 is connected to a manifold 20 through an extension tube 10. That is, containers 21, 22, 23, and 24 are connected to manifold 20 through conduits 25, 26, 27, and 29. The patient line is connected to manifold 20 through conduit 28. The containers include first dialysate container 21, second dialysate container 22, reservoir 23 with warming device 30, and drain container 24. Conduit 28 is connected to the patient 31. Each conduit is provided with swiching devices 32, 33, 34, 35, and 36. Each swiching device is described later.

First dialysate container 21 contains a dialysate of the first density. Second dialysate container 22 contains a dialysate of the second density. The dialysate in the first container and the dialysate in the second container are different in density.

The pressure applied to the patient's peritoneal cavity is set so as not to damage the peritoneal cavity. A dwell solution is discharged into drain container 24. The pressure in the patient's peritoneal cavity is monitored by an air-pressure sensor 14.

The operation of the APDS is explained below.

The dialysate of the first density in first dialysate container 21 is supplied to the patient through other containers by automated solution injection-discharge system 1, and drain is discharged out of the patient. The following is the method of supplying the patient with warmed dialysate of the first density in first dialysate container 21.

First, the swiching device 32 on conduit 25 is opened. A gas filling chamber 4 is exhausted from gas opening 9. Diaphragm 5 is inverted down to the side of the gas opening. As a result, dialysate in first dialysate container 21 is introduced into chamber 4 through conduit 25.

Second, the swiching device 34 is opened on conduit 27 connected to reservoir 23. A gas is introduced into chamber 4 from the gas opening 5, and then diaphragm 5 is inverted up to the side of the solution opening. As a result, dialysate dwelling in chamber 4 is supplied to reservoir 23.

Third, when dialysate warmed in reservoir 23 is injected into the patient's peritoneal cavity, swiching device 34 on conduit 27 is opened. Diaphragm 5 is inverted down to the side of the gas opening. As a result, the prescribed volume of dialysate is introduced into the chamber. Next, swiching device 35 is opened on conduit 28 connected to the patient 31. A gas is introduced into chamber 4 from the gas opening, and then diaphragm 5 is inverted up to the side of the solution opening. As a result, the dialysate dwelling in chamber 4 is injected into the peritoneal cavity of the patient 31 through conduit 28. By repeating the operation described above, the prescribed volume of dialysate is injected into the peritoneal cavity of the patient 31.

When the dialysate dwelling in the patient's peritoneal cavity for a determined period of time is discharged into drain container 24, swiching device 35 on conduit 28 is opened. Diaphragm 5 is inverted down to the side of the gas opening, as a result of which a drain is introduced into the diaphragm. Next, conduit 28 is closed, and only swiching device 36 is opened on conduit 29 connected to the drain container. Diaphragm 5 is inverted up to the side of the solution opening. As a result, the drain dwelling in the chamber is discharged into drain container 24.

When a dialysate, whose density is different from the dialysate in first dialysate container 21, is injected into the patient, second dialysate container 22 is used. As mentioned above, the dialysate in the second dialysate container is supplied to the chamber by the movement of the diaphragm. After that, the dialysate is discharged from the chamber into reservoir 23. As a result, the dialysate density is changed in the second dialysate container. Use of second dialysate container 22 depends on the dialytic treatment.

When 1000 cc of dialysate is to be injected into the patient with chamber 4 of 50 cc in volume, the operation described above is repeated 20 times.

For injecting dialysate into a patient, a peritoneal catheter is inserted into the patient's peritoneal cavity. Dialysate is injected into the peritoneal cavity or discharged from it through a conduit installed on a tube connected to the peritoneal catheter.

FIGS. 4(A) and (B) and FIG. 5 show the swiching device which opens only one conduit and closes the other conduits in the APDS of the present invention.

In FIGS. 4(A) and (B), closing gears 32 to 36 are provided with an interlocking cam 40, a thrust device 41, and a cradle 43 with a groove 42 which receives the head of thrust device 41. Cam 40 operates by the movement of a rotating shaft 44. The conduit is opened and closed by the up-and-down motion of the thrust device which follows the interlocking cam. Each cam operates independently.

FIG. 4(A) shows an opened conduit. FIG. 4 (B) shows a closed conduit. In Figure (A), cam 40 operates by the movement of rotating shaft 44. Thrust device 41 moves up to push up the conduit. As a result, the head of the thrust device is fitted into groove 42 of cradle 43 to close the conduit.

In an APDS with five conduits 25, 26, 27, 28, and 29 shown in FIG. 5, one rotating shaft 44 is preferably equipped with not more than three interlocking cams 40. This is because when an opened conduit is closed by either a positive or a negative shaft rotation, one of the other conduits can be opened.

When one rotating shaft is equipped with four or more interlocking cams, however, it is difficult to open the desired conduit with the other conduits remaining closed. In other words, when user tries to open the conduit by one rotating shaft with more than two out-of-phase interlocking cams, the other out-of-phase conduits are undesirably opened. When three out-of-phase cams are installed on one rotating shaft, and the first opened cam is closed by rotating the shaft positively or negatively, the third (or second) closed cam can be opened without opening the second (or third) cam. When one conduit closing gear is installed on one rotating shaft, the number of rotating shafts increases, which makes the system and control regulation complicated.

The five units of swiching device are set on rotating shafts so as to be able to open only one of the conduits (25, 26, 27, 28, and 29) by the rotation of shaft 44. One conduit is set up to be opened by the rotation of shaft 44. Three cams in the first row are installed, with a 120 degree phase difference, on the first rotating shaft 44. Two cams in the second row are installed, with a 120 to 180 degree phase difference, on the second rotating shaft 44.

When the second dialysate container is not used, four conduits are used. In this case, desirably, two cams in the first row are installed on the first rotating shaft with a 120 to 180 degree phase difference, and two cams in the second row are installed on the second rotating shaft with a 120 to 180 degree phase difference. Moreover, three conduit swiching device may be installed on one rotating shaft, and one conduit swiching device may be installed on the other shaft.

It is also desirable that a sensor be set up near the cam for determining the cam's position and/or direction of rotation. The sensor is a photo-sensor or an encoder which can detect the rotating position. The photo-sensor confirms a position of the cam. The cam's direction of rotation is then determined in order to move the thrust device to the clamped conduit.

FIG. 6 shows an APDS using a solution supply and suction system which is equipped with both a piston and a cylinder to suck and supply a peritoneal dialysate and a drain from/to a patient's peritoneal cavity, instead of using an automated solution injection-discharge system equipped with a diaphragm.

In this case, dialysate container 21 is connected to the end of manifold 20 through conduit 25, and reservoir 23 is connected to the end of manifold 20 through conduit 27. When the dialysate in dialysate container 21 is introduced into reservoir 23, swiching device 32 on conduit 25 is opened, and the prescribed volume of the dialysate is introduced into cylinder 46 by driving a piston 45. Next, conduit 25 is closed, and closing gear 34 on conduit 27 connected to reservoir 23 is opened. The dialysate sucked into the cylinder above by pressing the piston is introduced into reservoir 23. By repeating the above operation, the required volume of dialysate is reserved in reservoir 23. For example, when 1000 ml of dialysate is supplied using a 100 ml cylinder, the above operation should be repeated 10 times.

To inject dialysate warmed in reservoir 23 into a patient's peritoneal cavity, swiching device 34 on conduit 27 is opened, and the prescribed volume of dialysate is introduced into cylinder 46 by driving piston 43. Then conduit 27 is closed, and swiching device 36 on conduit 28 connected to the patient's peritoneal cavity is opened. The prescribed volume of dialysate sucked by pressing piston 43 is introduced into the patient's peritoneal cavity. By repeating the above operation, the required volume of dialysate is injected into the patient's peritoneal cavity.

To discharge the dwell solution in a patient's peritoneal cavity, swiching device 35 on conduit 28 is opened, and the dwell solution in the peritoneal cavity of the patient 31 is sucked into cylinder 46. Then, conduit 28 is closed, and swiching device 35 on conduit 29 is opened. The dwell solution sucked into the cylinder by pressing piston 43 is discharged into drain container 24. With the above operation repeated, the dwell solution is discharged into the drain container while preventing the pressure in the peritoneal cavity from being negative to the extent that a living body might be damaged.

Since the dwell solution is discharged into the drain container while preventing the pressure in the peritoneal cavity from being excessively negative, use is made of a peritoneal catheter or a conduit connected to the extension tube of a catheter that can be closed by, for example, a negative pressure of 110 mmHg or more and expanded by, for example, a positive pressure of 140 mmHg or more. The peritoneal catheter and the conduit mentioned above can desirably stop the application of excessive pressure to the peritoneal cavity or can alleviate pressure. The above conduit, or at least a part of the conduit, is preferably made from a flexible thin film. Moreover, the pressure in the cylinder is preferably measured by an overload sensor installed at the end of the piston.

When a solution is discharged from each conduit except the peritoneal catheter inserted into a patient's peritoneal cavity and the conduit connected to the extension tube of the catheter, or when a solution is introduced into each conduit, the movement speed of a piston is 400 to 600 ml/min. On the other hand, when a solution is introduced into peritoneal catheter inserted into a patient's peritoneal cavity and the conduit connected to the extension tube of the catheter, the movement speed of a piston is 10 to 300 ml/min., preferably, 200 ml/min, which does not damage the peritoneal cavity. The volume of the cylinder is 30 to 200 ml, preferably, 50 to 100 ml.

That is, when a solution is discharged from a peritoneal cavity, the movement speed of piston is ordinary 10 to 200 ml/min, preferably, 150 ml/min. When a solution is introduced into a peritoneal cavity, the movement speed of piston is ordinary 20 to 400 ml/min, preferably, 300 ml/min.

In order to shorten the fill and drain time, it is preferable that the speed of piston movement for discharging a solution from each conduit except a peritoneal catheter and the conduit connected to the extension tube of the catheter, or for infusing a solution into each conduit be faster than the speed of piston movement for supplying a solution in a peritoneal catheter and the conduit connected to the extension tube of the catheter.

When a solution is supplied from other conduits, or when a solution is discharged into other conduits, the speed of piston movement is set to a high value, for example, 400 to 600 ml/min, in order to shorten the fill and drain time.

In the above case, a cylinder and a piston are paired, but plural sets, for example two sets of cylinders and pistons may also be used, as shown in FIG. 7. The use of two such sets can prevent waiting time for sucking and discharge of dialysate or drain from a patient's peritoneal cavity, and can lessen the effect of intermittent transit. In other words, while one set of a cylinder and a piston sucks, the other set can discharge.

In FIG. 7, two cylinders are paired with a belt 47. Cylinder flanges 48 are located at the back end of the cylinders. Piston flanges 49 are located at the back end of the pistons.

With the same operation as described above, a solution is sucked and introduced between each container. In FIG. 7, each conduit is branched into two, and all the branched conduits are respectively provided with swiching device.

A piston is desirably asepticized. As shown in FIG. 8, a piston is asepticized by being covered from cylinder flange 48 and piston flange 49 with a flexible accordion-fold aseptic cover 50. Or, as shown in FIG. 9, both a cylinder and a piston are completely covered with a stretchable cover 51; for example, a rubber cover.

FIG.10 shows an APDS using a solution supply and suction system which is equipped with a flexible bag to suck and supply peritoneal dialysate and drain from a patient's peritoneal cavity, instead of using the automated solution injection-discharge system.

In an APDS using the solution supply and suction system, a bag 53 is compressed by pressurizing a sealed container 52. As a result, a dialysate in the bag or a drain from a patient's peritoneal cavity can be sent. By depressurizing the chamber, a negative pressure is applied to the bag. As a result, a dialysate or a drain from a patient's peritoneal cavity can be sucked into the bag.

In the same operation as mentioned above, when a dialysate is supplied from dialysate container 21 to reservoir 23, swiching device 32 on conduit 25 is opened, and sealed container 52 is depressurized to introduce dialysate from the dialysate container into flexible bag 53. Then, swiching device 34 on conduit 27 is opened to pressurize the sealed container, and the solution in the flexible bag is sent to reservoir 23 and is warmed by warming device 30. Swiching device 34 on conduit 27 is opened to introduce the dialysate into the flexible bag. Next, conduit swiching device 35 is opened to inject the dialysate in the flexible bag into the patient's peritoneal cavity.

With the automated solution injection-discharge system of the present invention, an excessive injection or discharge (suction) which might burden a living body can be prevented and a dialysate and dwell solution can be accurately injected and discharged, because the chamber equipped with a diaphragm quantitatively performs solution injection and discharge. Moreover, the stroke of the air cylinder can quantitatively perform injection and discharge.

With the automated solution injection-discharge system of the present invention, because of its function as a metering pump, when the system is set up with an APDS, the system counts the amount of solution supplied without weighing out supplied dialysate or discharged dwell solution. Additionally, a position detecting sensor locates a piston to determine the quantity of supplied solution. Therefore, the automated solution injection-discharge system of the present invention does not need to be equipped with an expensive gravimetric load cell.

If only a dialysis flow pathway is set up with an APDS equipped with the automated solution injection-discharge system of the present invention, the APDS can automatically select, close, and open flow channels, and can perform almost all operations as necessary to measure, warm, introduce, and discharge a solution, or as necessary to replace a solution such as priming. Accordingly, accidents resulting from operating mistakes can be prevented, and troublesome manual operations can be eased. A sight- or hand-impaired patient can use the system safely.

Furthermore, the APDS of the present invention is relatively simple in structure and low in cost, because the APDS uses conduit swiching device such as a combination of interlocking cams and thrust devices, enabling optional plural conduits can be opened by the rotation of a shaft.

The APDS of the present invention can safely and automatically inject and discharge a solution, because a dwell solution can be discharged while preventing the pressure in the peritoneal cavity from being sufficiently negative to damage a living body.

What is claimed is:

1. An automated peritoneal dialysis system, comprising:
   a manifold;
   a first dialysate container connected through a first dialysate supply line to said manifold;
   a reservoir connected through a conduit to said manifold;
   a warming device connected to said reservoir, for warming dialysate in the reservoir;
   a drain container connected through a drain line to said manifold;
   a patient line, for connection to the peritoneal cavity of a patient, connected to said manifold;
   switching devices on said first dialysate supply line, said conduit, said patient line and said drain line; and
   a cylinder and a piston connected to said manifold, for pumping fluid through said manifold.

2. The automated peritoneal dialysis system of claim 1, further comprising:
   a second dialysate container for containing a dialysate of different density than that of the first dialysate container;
   a second dialysate supply line connected to said manifold; and
   a switching device on said second dialysate supply line.

3. The automated peritoneal dialysis system of claim 1, further comprising: automatic means for driving said piston and for controlling said switching devices.

4. The automated peritoneal dialysis system of claim 3, said automatic means for driving the piston being capable of drive speeds of 10 to 600 mL/min.

5. The automated peritoneal dialysis system of claim 1, said cylinder further comprising:
   a cylinder flange at the end of the cylinder opposite the connection to the manifold.

6. The automated peritoneal dialysis system of claim 5, said cylinder further comprising:
   a piston flange on the end of the piston outside the cylinder.

7. The automated peritoneal dialysis system of claim 6, said cylinder further comprising:
   a flexible, accordion-fold aseptic cover over the piston between the cylinder flange and the piston flange.

8. An automated peritoneal dialysis system, comprising:
   a first manifold and a second manifold;
   a first dialysate container connected through two first dialysate supply lines to said first and second manifolds, respectively;
   reservoir connected through two conduits to said first and second manifolds, respectively;
   a warming device connected to said reservoir, for warming dialysate in the reservoir;
   a drain container connected through two drain lines to said first and second manifolds, respectively;
   a patient line, for connection to the peritoneal cavity of a patient, connected to said first and second manifolds;
   switching devices on said first dialysate supply lines, said conduits, said drain lines and the connections between said first and second manifolds and said patient line;
   a first cylinder and a first piston connected to said first manifold; and
   a second cylinder and a second piston connected to said second manifold.

9. The automated peritoneal dialysis system of claim 8, further comprising:
   a belt wrapped around said first and second cylinders.

10. The automated peritoneal dialysis system of claim 8, further comprising:
    automatic means for driving said first and second pistons and for controlling said switching devices.

11. The automated peritoneal dialysis system of claim 10, said automatic means for driving the pistons being capable of piston drive speeds of 10 to 600 mL/min.

12. The automated peritoneal dialysis system of claim 10, said automatic means for driving the pistons being capable of driving the first piston for discharging while the second piston is driven for sucking.

13. The automated peritoneal dialysis system of claim 10, further comprising:
    a second dialysate container for containing a dialysate of different density than that of the first dialysate container;
    second dialysate supply lines connecting said second dialysate container to said first and second manifolds; and
    switching devices on said second dialysate supply lines.

14. The automated peritoneal dialysis system of claim 8, said cylinder further comprising:
    two cylinder flanges, one of the cylinder flanges at the end of each cylinder opposite the connection to the manifold.

15. The automated peritoneal dialysis system of claim 14, said cylinder further comprising:
    two piston flanges, one of the piston flanges on the end of each piston outside the cylinder.

16. The automated peritoneal dialysis system of claim 15, said cylinder further comprising:
    a flexible, accordion-fold aseptic cover over each piston between the cylinder flange and the piston flange.

17. An automated peritoneal dialysis system, comprising:
    a manifold;

a first dialysate container connected through a first dialysate supply line to said manifold;

a reservoir connected through a conduit to said manifold;

a warming device connected to said reservoir, for warming dialysate in the reservoir;

a drain container connected through a drain line to said manifold;

a patient line, for connection to the peritoneal cavity of a patient, connected to said manifold;

switching devices on said first dialysate supply line, said conduit, said patient line and said drain line; and an automated solution injection-discharge system, said automated solution injection-discharge system comprising:
  a chamber having a solution opening connected to the manifold and a gas opening;
  a diaphragm in said chamber between said solution opening and said gas opening; and
  an air cylinder and a piston connected to said gas opening, for applying pressure to said diaphragm.

18. An automated peritoneal dialysis system, comprising:

a manifold;

a first dialysate container connected through a first dialysate supply line to said manifold;

a reservoir connected through a conduit to said manifold;

a warming device connected to said reservoir, for warming dialysate in the reservoir;

a drain container connected through a drain line to said manifold;

a patient line, for connection to the peritoneal cavity of a patient, connected to said manifold;

switching devices on said first dialysate supply line, said conduit, said patient line and said drain line; and an automated solution injection-discharge system, said automated solution injection-discharge system comprising:
  a chamber having a solution opening connected to the manifold and a gas opening;
  a diaphragm in said chamber between said solution opening and said gas opening; and
  an air cylinder and a piston connected to said gas opening, for applying pressure to said diaphragm, the volume of said air cylinder being 1.4 to 2.0 times the volume of said chamber.

19. The automated peritoneal dialysis system of claim 18, further comprising: an air pressure sensor in the connection between the air cylinder and the gas opening.

20. The apparatus of claim 18, further comprising:

a second dialysate container for containing a dialysate of different density than that of the first dialysate container;

a second dialysate supply line connected to said manifold; and a switching device on said second dialysate supply line.

21. The automated peritoneal dialysis system of claim 18, further comprising:

a photoencoding position detecting sensor for determining the position of said piston in said cylinder.

22. The automated peritoneal dialysis system of claim 18, further comprising:

a temperature sensor in the connection between the air cylinder and the gas opening.

23. An automated peritoneal dialysis system, comprising:

a manifold;

a first dialysate container connected through a first dialysate supply line to said manifold;

a reservoir connected through a conduit to said manifold;

a warming device connected to said reservoir, for warming dialysate in the reservoir;

a drain container connected through a drain line to said manifold;

a patient line, for connection to the peritoneal cavity of a patient, connected to said manifold;

switching devices on said first dialysate supply line, said conduit, said patient line and said drain line; and an automated solution injection-discharge system, said automated solution injection-discharge system comprising:
  a chamber having a solution opening connected to the manifold and a gas opening;
  a diaphragm in said chamber between said solution opening and said gas opening;
  an air cylinder and a piston connected to said gas opening, for applying pressure to said diaphragm; and
  an automated conduit switching device for controlling said switching devices, said automated conduit switching device comprising:
    a first rotating shaft;
    an interlocking cam on the first rotating shaft;
    a thrust device which moves up and down with rotation of the interlocking cam; and
    a cradle which receives the head of the thrust device.

24. The automated peritoneal dialysis system of claim 23, further comprising:

a second rotating shaft having an interlocking cam.

25. The automated peritoneal dialysis system of claim 24, said first rotating shaft having a total of three interlocking cams and said second shaft having a total of two interlocking cams.

26. The automated peritoneal dialysis system of claim 25, the three interlocking cams of the first rotating shaft having a phase difference of 120°, and the two interlocking cams of the second rotating shaft having a phase difference of 120° to 180°.

27. An automated peritoneal dialysis system, comprising:

a manifold;

a first dialysate container connected through a first dialysate supply line to said manifold;

a reservoir connected through a conduit to said manifold;

a warming device connected to said reservoir, for warming dialysate in the reservoir;

a drain container connected through a drain line to said manifold;

a patient line, for connection to the peritoneal cavity of a patient, connected to said manifold;

switching devices on said first dialysate supply line, said conduit, said patient line and said drain line;

a cylinder and a piston connected to said manifold, for pumping fluid through said manifold; and an automated conduit switching device for controlling said switching devices, said automated conduit switching device comprising:
  a first rotating shaft;
  an interlocking cam on the first rotating shaft;
  a thrust device which moves up and down with rotation of the interlocking cam; and
  a cradle which receives the head of the thrust device.

* * * * *